United States Patent [19]

Milijasevic et al.

[11] Patent Number: 4,938,231
[45] Date of Patent: Jul. 3, 1990

[54] DEFIBRILLATOR ELECTRODE

[75] Inventors: Zoran Milijasevic, Elanora Heights; Loraine K. Holley, Rockdale; Michael Skalsky, Waverley, all of Australia

[73] Assignee: Telectronics N.V., Netherlands

[21] Appl. No.: 274,669

[22] Filed: Nov. 21, 1988

Related U.S. Application Data

[63] Continuation of Ser. No. 790,166, Oct. 22, 1985, abandoned.

[51] Int. Cl.$^5$ .............................................. A61N 1/36
[52] U.S. Cl. ............................. 128/784; 128/419 D; 128/785
[58] Field of Search ......................................... 128/785

[56] References Cited

U.S. PATENT DOCUMENTS

| | | | |
|---|---|---|---|
| 1,973,387 | 9/1934 | Neymann et al. | 128/798 |
| 2,065,295 | 12/1936 | Sullivan | 128/798 |
| 2,985,172 | 5/1961 | Jones | 128/784 |
| 3,788,329 | 1/1974 | Friedman | 128/419 P |
| 4,030,509 | 6/1977 | Heilman et al. | 128/419 D |
| 4,161,952 | 7/1979 | Linney et al. | 128/786 |
| 4,270,549 | 6/1981 | Heilman | 128/784 |
| 4,291,707 | 9/1981 | Heilman et al. | 128/419 D |
| 4,314,095 | 2/1982 | Moore et al. | 128/642 |
| 4,355,646 | 10/1982 | Kallok et al. | 128/786 |
| 4,384,582 | 5/1983 | Watt | 128/798 |
| 4,620,550 | 11/1986 | Doroshuk | 128/785 |

OTHER PUBLICATIONS

Schuder et al., "Relationship Between Electrode Geometry and Effectiveness of Ventricular Defibrillation in the Dog . . . ", Cardiovascular Research, 1973, 7, pp. 629–637.
Santel et al., "Implantable Defibrillator Electrode Systems: A Brief Review", PACE, vol. 8, Jan.-Feb. 1985, pp. 123–131.
Babbs et al., "Effects of Myocardial Infraction on Catheter Defibrillation Threshold", Medical Instrumentation, vol. 17, No. 1, Jan.-Feb. 1983, pp. 18–20.
Ewy et al., "Electrode System for Permanent Implantable Defibrillators: Transvenous Catheter and Subcutaneous Plate Electrodes", Medical Instrumentation, vol. 12, No. 5, Sept.-Oct. 1978, pp. 296–300.
Schuder et al., "Ventricular Defibrillation in the Dog with a Bielectrode Intravascular Catheter", Arch. Inter Med., vol. 132, Aug. 1973, pp. 286–290.
Ewy et al., "Electrode Catheter for Transvenous Defibrillation", Medical Instrumentation, vol. 10. No. 3, May-Jun. 1976, pp. 155–158.
Rubin et al., "Automatic Defibrillation and Pacing with a Transvenous Electrode", Report to U.S. Army Medical Research and Development Command (DAMD-17-74-C-1408) undated, pp. 427–430.

Primary Examiner—Francis Jaworski
Attorney, Agent, or Firm—Finnegan, Henderson, Farabow, Garrett & Dunner

[57] ABSTRACT

A patch-type defibrillator electrode for direct contact with the heart has a thin, flat, flexible generally circular mesh or foil conductive member with a pattern of slits for enabling continuous contact with the three dimensional, time-varying heart surface topography. The slit pattern includes two pairs of non-intersecting semicircular slits oriented along mutually perpendicular axes, and interior portions of the conductive member are flexibly movable in a direction normal to the plane member and are flexibly tiltable about the axes to provide the conforming contact. The slits may also be radial slits which do not meet at the center so the leaves of conductive members are independently mobile with respect to every other leaf. A Dacron envelope having a thrombus formation inhibiting agent surrounds the conductive member including the peripheral edges to reduce the risk of tissue burning from current supplied to the center of the conductive member by an electrode lead.

33 Claims, 4 Drawing Sheets

DEFIBRILLATOR ELECTRODE

This application is a continuation of application Ser. No. 790,166, filed Oct. 22, 1985 now abandoned.

BACKGROUND OF THE INVENTION

1. Field of the Invention

The present invention relates to electrodes implantable in living beings and, more particularly, to improved flexible defibrillator electrodes for attaching directly to the surface of the heart muscle, or over pericardial tissue.

2. Description of the Prior Art

It is well known that cardiac arrhythmias such as atrial fibrillation ("A.F.") and ventricular fibrillation ("V.F.") can be overcome by electrical energy applied across the myocardium. In situations where A.F. and V.F. does occur, defibrillation is accomplished by external paddles placed on the chest or, during surgery, internal paddles may be placed directly onto the heart, usually across the ventricles. These procedures have become fairly common and have proven to be quite effective.

More recently, implantable defibrillators have been suggested for automatic sensing and control of cardiac arrhythmias. Such defibrillators require electrodes which may be in contact with the heart surface or are intravascular catheters or are a combination of these.

Defibrillator electrodes have so far been of two types, namely endocardial types with large surface areas usually in the form of rings and located in the Superior Vena Cava ("SVC"), and patch-type electrodes to be placed on the external wall of the heart. The endocardial electrodes are implanted through a vein in the same manner as pacemaker electrodes and are positioned in the SVC area.

The patch-type electrodes known to the art have been of varied types, usually rectangular in shape with sutures used for fixing to the heart. In general, the prior art patch-type electrodes have been relatively stiff devices which have difficulty in maintaining conforming contact with the heart which presents a three dimensional, time-varying surface topography. One patch-type prior art electrode is made from a titanium mesh but is nonetheless relatively inflexible. Most common implant techniques require thoracic surgery to expose the epicardium on which the electrodes are sutured. The implant methods are awkward and difficult and thus it is very important to have an electrode that maintains conforming contact with the heart surface to preclude corrective surgery.

SUMMARY OF THE INVENTION

In accordance with the invention as embodied and broadly described herein, the apparatus for use as an electrode adapted for implantation in a patient comprises a tissue-contacting member including a sheet of electrically conductive, flexible material having a generally unflexed planar shape, and a plurality of elongated slits arranged in a pattern in the sheet. A part of at least one interior portion of the sheet defined by the pattern is flexibly movable in a direction perpendicular to the plane of the sheet past sheet portions separated from the first portion by the pattern of slits to enable contacting the tissue member to conform to tissue having a three dimensional, time-varying surface topography.

Preferably, the one interior portion defined by the slit pattern also is flexibly tiltable about at least one axis lying in the plane of the sheet.

It is also preferred that the pattern of slits includes a first pair of complementary slits extending generally in a first sheet direction. A part of the sheet portion central to the pair of slits is flexibly movable past first sheet portions separated from the central sheet portion by the first pair of slits, in a direction normal to said sheet proximal and distal surfaces.

It is further preferred that the shape of each slit of the first pair and second pair of slits is semicircular, and the shape of the central sheet portion is circular.

The pattern also includes a second pair of complementary slits extending generally in a second sheet direction. The structural unit comprised of the first pair of slits, the included central sheet portion, and the first separated sheet portion is positioned between the second pair of slits, and a part of the structural unit is flexibly movable in the normal direction past a second sheet portion separated from the unit by the second pair of slits.

It is still further preferred that the apparatus include a continuously porous non-conductive layer covering the proximal and distal sheet surfaces and enveloping the peripheral edges of the sheet, to reduce the risk of tissue burning, and that the porous layer contains a biologically active agent to combat thrombus formation.

DESCRIPTION OF THE PREFERRED EMBODIMENT

Figure 1:
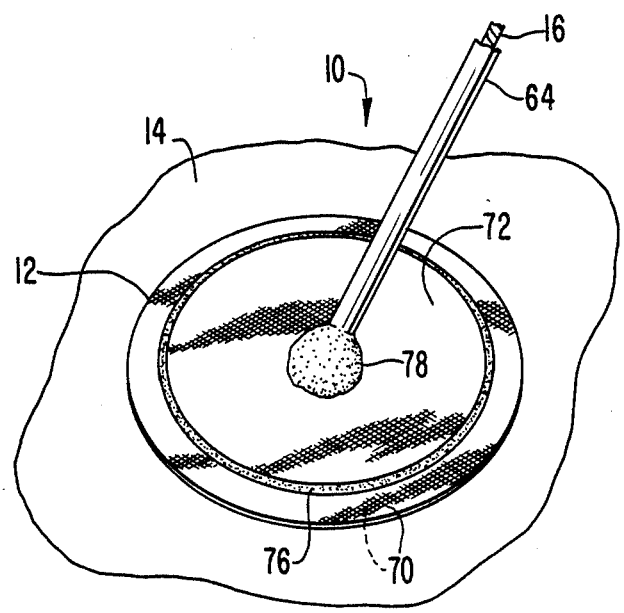
FIG. 1 is a perspective schematic view of an electrode made in accordance with the present invention and contacting a tissue body.

Reference will now be made in detail to the present preferred embodiment of the invention, an example of which is illustrated in the accompanying drawing. An example of the preferred embodiment of an electrode made in accordance with the present invention and especially suited for use as a defibrillator electrode is shown in FIG. 1 and is designated generally by the numeral 10. Electrode 10 has a generally planar member 12 for contacting a suitable tissue body such as body 14 to be stimulated by an electric current. In the example shown in FIG. 1, electric current is supplied to planar member 12 by an electrical conductor 16 from a source (not shown) which can be, for instance, an extracorporeal power supply.

As is apparent from the preceeding discussion, one of the preferred applications for the electrode of the present invention is for an implantable defibrillator electrode for direct attachment to the heart muscle. The heart muscle presents not only a three dimensional surface topography to be contacted by the electrode, but a time-varying surface shape as a consequence of the pumping action of the heart. Thus, it becomes especially important in such applications to have the electrode be able to continuously conform to the surface shape without impeding pumping action. The electrode of the present invention has been found to provide such continuously conforming contact by means which will be discussed in greater detail hereinafter.

In accordance with the present invention, the electrode adapted for implantation in a patient includes a tissue-contacting member formed from a sheet of electrically conductive, flexible material. As embodied herein, and with reference to FIGS. 2 and 3, tissue contacting member 12 includes a circular sheet element 20 having a distal surface 22 (see FIGS. 3A and 7) for contacting tissue body 14 and a proximal surface 24. Sheet 20 is preferably formed from a thin, fine woven mesh of a conductive material such as titanium, platinum, MP35N, stainless steel, carbon, or other bio-compatible conductive material. Electrodes according to the present invention and having a tissue contact member as shown in FIG. 3 have been fabricated using 0.036 mm 316L stainless steel wire in a 0.075 mm thick mesh having 325 wires/inch. These electrodes have been successfully implanted in dogs. However, a mesh fabricated from platinum/10% iridium is specifically contemplated for future human and animal implants, or any other material which is conductive and biocompatible could be used. Conductive foil also can be used for sheet element 20. The mesh or foil is welded along all cut edges, such as peripheral edge 26, to remove sharp points. This welding operation is especially important if a mesh material is used. Other methods to remove sharp joints such as laser cutting, spark erosion etc. could also be used. In the undeformed or unflexed state, sheet element 20 is generally planar, as is shown in FIGS. 3 and 4.

Further in accordance with the present invention, the electrically conductive flexible sheet includes a plurality of elongated slits arranged in a pattern. Importantly, a part of an interior portion of the sheet defined by the pattern is flexibly movable in a direction perpendicular to the plane of the sheet. Movement of the interior portion part past the sheet portion separated by the pattern of slits enables the contacting member to conform to the three dimensional tissue surface and accommodate time-varying surface changes.

Figure 3A:
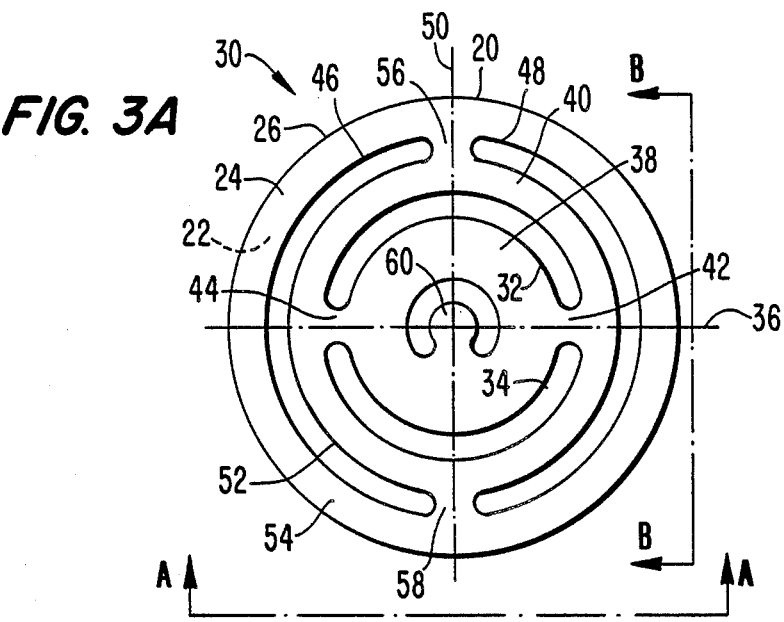
FIG. 3A is a top view of the sheet conductor element of the electrode shown in FIG. 1.
Figure 3B:
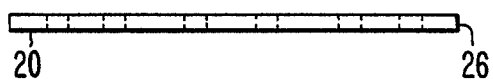
FIG. 3B is a side view of the sheet conductor element shown in FIG. 3A viewed in the direction AA, in an unflexed state.
Figure 4:
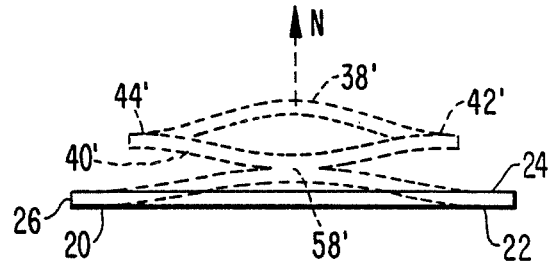
FIG. 4 is a side view of the sheet conductor element shown in FIG. 3A viewed in the direction AA, with flexible translation of parts thereof shown in dotted lines.

As embodied herein, and with reference to FIGS. 3 and 4, a slit pattern designated generally by the numeral 30 is formed in sheet 20 such as by stamping, cutting, etc. Pattern 30 includes an inner pair of complementary semicircular slits 32, 34 extending generally in the direction designated by axis 36 lying in the plane of sheet 20. Complementary slits 32, 34 define and partially enclose a circular, central sheet portion 38 to which conductor 16 is attached in a manner that will be explained in more detail subsequently. Slits 32, 34 are non-intersecting and, as a result, central sheet portion 38 is connected by a pair of opposed web portions 42, 44 to annular sheet portion 40 which is separated from central sheet portion 38 by slits 32, 34. Slits 32, 34 thereby enable a substantial part of central sheet portion 38 to move in the direction normal to sheet surfaces 22, 24 (into and out of the paper in FIG. 3A) and past the adjacent parts of annular sheet portion 40. Of course, the parts of central sheet portion 38 immediately adjacent web portions 42, 44 are constrained by the respective web portions to move together with the adjacent parts of sheet portion 40.

Preferably, and as embodied herein, slit pattern 30 includes a second pair of complementary slits 46, 48 of semicircular shape extending in a direction at an angle to the direction of slits 32, 34. With continued reference to FIG. 3A, slits 46, 48 extend generally in the direction of axis 50 which is perpendicular to the direction of axis 36. Slits 46, 48 serve to define and partially close the sub-unit (designated by the numeral 52) of sheet 20 that includes annular portion 40, slits 32, 34, and central portion 38. Sub-unit 52 is connected to peripheral sheet portion 54 by a pair of opposing web portions 56, 58. By virtue of the flexibility of sheet 20 and the arrangement of the slits 46, 48, a major portion of sub-unit 52 can flexibly move in the normal direction past adjacent parts of peripheral sheet portion 54, in response to the changing shape of the contacted tissue, in a manner similar to the previously described movement of central portion 38 past annular portion 40.

Importantly, and as best seen in FIG. 4, the combination of slit pairs 32, 34 and 46, 48 enables the interior of sheet 20 to flexibly deform to accommodate changes in the curvature of tissue body 14. The mode of flexing deformation of the interior portion of sheet 20 is not unlike that found in Japanese lantern type hanging ornaments. In FIG. 4, the deformed stage shown in dotted lines is exaggerated for clarity, with prime numerals designating the deformed or "flexed" respective parts of sheet 20.

It is also preferred that the width of each of the web portions 42, 44 and 56, 58 be made as small as possible consistent with the need to maintain structural integrity during flexing and to have sufficient conductor volume to distribute current without creating a tissue burning condition. For relatively thin webbed portions, the respective interconnected sections of sheet 20 can twist or "tilt" to a limited extent with respect to one another about an axis drawn through the respective pairs of webs. This flexible tilting relative movement increases the ability of sheet 20 to conform to a three dimensional shape, especially a time-varying three dimensional shape, such as the surface of the beating heart.

Figure 5:
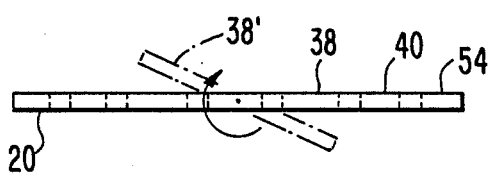
FIG. 5 is a side-view of the sheet conductor element shown in FIG. 3A viewed in the direction BB, with flexible tilting of a part thereof depicted with dotted lines.
Figure 6:
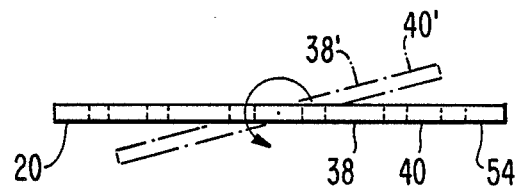
FIG. 6 is a side view of the sheet conductor element shown in FIG. 3A viewed in a direction AA, with flexible tilting of another part thereof depicted with dotted lines.

For example, and as best seen in FIGS. 3A and 5, central portion 38 can tilt relative to both intermediate annular portion 40 and peripheral sheet portion 54, about axis 36 drawn through web portions 42, 44 (tilt orientation represented by 38'). In a similar fashion, and with respect to FIGS. 3A and 6, intermediate annular sheet portion 40 and included central portion 38 can tilt relative to peripheral sheet portion 54, about axis 50 which is perpendicular to axis 36 and runs through web portions 56, 58. Although not shown in FIG. 6, central portion 38 could simultaneously tilt with respect to annular portion 40. Also not shown, the angular directions of tilt can be reversed and the flexing movement in the normal direction can be superimposed on the tilting movement.

The several degrees of freedom resulting from the construction according to the present invention was found to provide a remarkable degree of conformity between sheet 20 and a beating heart muscle. The test sample included a sheet 20 manufactured from 0.036 mm wire woven into a 0.075 mm thick 325/inch mesh. Sheet 20 had a circular shape as depicted in FIG. 3A with an outside diameter of 38 mm, and having inner semicircular slits 32, 34 on a 20 mm diameter and outer semicircular slits 46, 48 on a 30 mm diameter. The slits were each about 2 mm wide, and all webb portions were about 2.5 mm in width.

Figure 7:
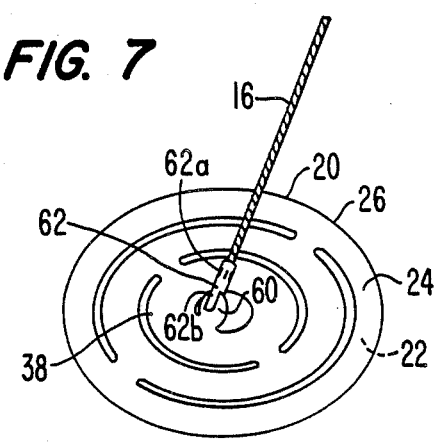
FIG. 7 shows further details of parts of the electrode shown in FIG. 1.
Figure 8:
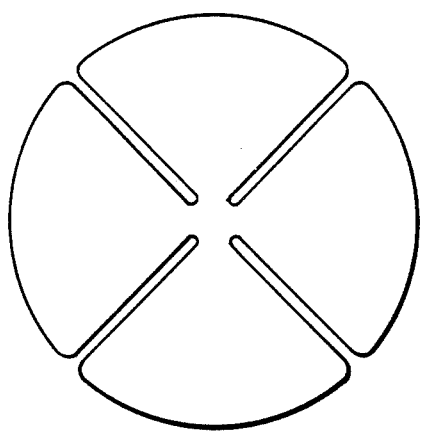
FIG. 8 is the top view of a flexible sheet conductor element in the shape of a four leaf clover.
Figure 9:
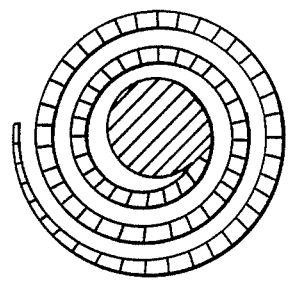
FIG. 9 is the top view of a flexible, sheet conductor element in the shape of a spiral.
Figure 10:
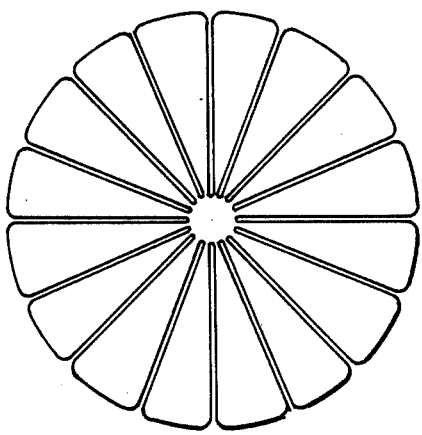
FIG. 10 is the top view of a flexible sheet conductor element with a multitude of radial slits.
Figure 11:
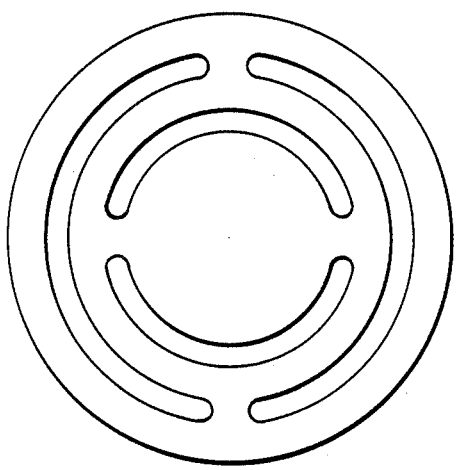
FIG. 11 is the top view of a flexible sheet conductor element which is similar to that in FIG. 3A but has the inner lip missing.

Further details of the present preferred embodiment of an electrode made in accordance with the present invention will now be described with reference to FIGS. 1, 2 and 7. Specifically, conductor 16 which should be formed from a low resistance material (e.g. platinum, platinum/iridium, DBS tungsten etc.) and in a fatigue resistant form such as a multifilar helix or ribbon, is connected to tab portion 60 formed in sheet 20, by a titanium connector pin 62. Tab portion 60 is located in the central sheet portion 38 and, because of the concentric arrangement of the remainder of sheet 20, a more even distribution of any mechanical stress imparted to sheet 20 can be achieved compared to an attached location for instance on peripheral portion 54. The shape of sheet 20 need not be circular but can be elliptical or even rectangular with well-rounded corners. Pin 62 is swaged to conductor 16 at pin end 62a and is riveted to tab portion 60 at pin end 62b. Silicone insulative sheath 64 (FIGS. 1 and 2) is disposed around conductor 16.

Figure 2:
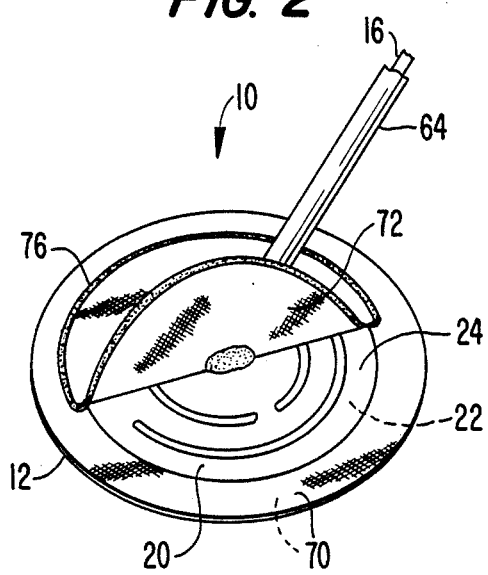
FIG. 2 is a perspective view of the electrode shown in FIG. 1 with a cover member folded back to show internal details.

As embodied herein and with reference now to FIGS. 1 and 2, electrode 10 includes porous dacron layer 70 covering distal surface 22 and enveloping edge 26 of sheet 20. Layer 70 helps prevent severe tissue burning at the peripheral edge, which has the highest electrical field intensity. Porous layer 70 also provides for tissue ingrowth, helping to secure electrode 10 to tissue, particularly when non-woven foil material is used for sheet 20. It is also preferred that proximal surface be enclosed by a porous layer 72 to provide a complete envelope for electrode 10. As embodied herein, and as best seen in FIGS. 1 and 2, Dacron layer 72 covers proximal surface 24 and is attached to the porous layer 70 by bead 76 of silicone glue. Layer 72 can be less porous than layer 70 because firm tissue attachment to proximal surface 24 is not critical. Bead 78 of silicon glue or similar material is used to attach insulated sheath 64 to Dacron layer 72.

Figure 13:
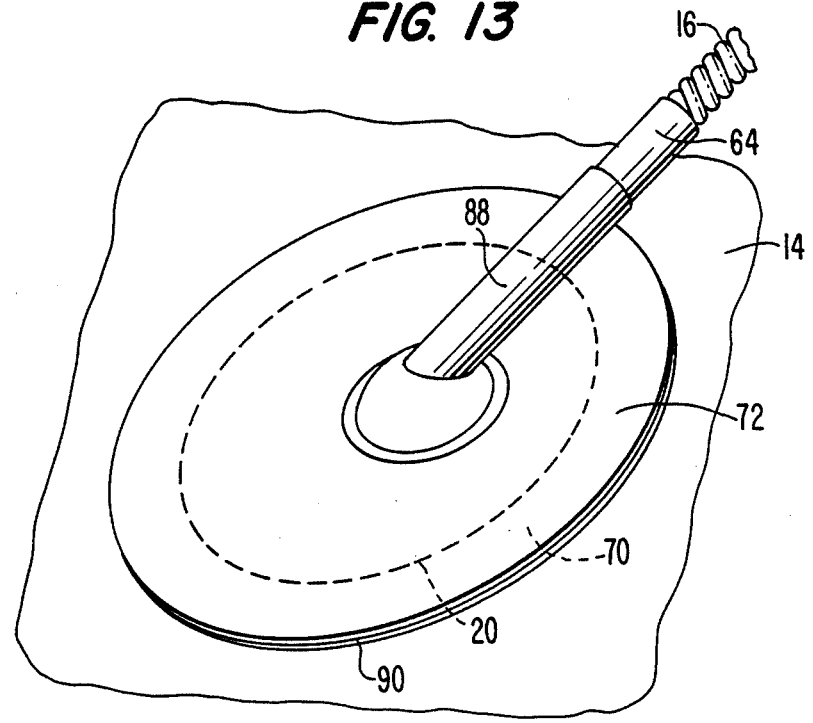
FIG. 13 is a perspective view of a thin highly flexible patch electrode.

The main theme behind this invention is the idea of a flexible electrode patch. Although a specific electrode design has been mentioned, the spirit of this invention is such that the flexibility of the electrode is of main concern rather than the actual shape. The patch 20 described thus far in this invention is only one of many other shapes which could be used to achieve the desired effect. Some of the other shapes are shown in FIGS. 8 to 11. The flexibility of the patch can be increased with thinner wire in the construction of the mesh, and for best flexibility, a conductive cloth should be used. The cloth could be made from a conductive, biocompatible material such as platinum, platinum/iridium, carbon, etc. Such a patch is depicted in FIG. 13. The conductor 16 is attached to the flexible patch 20 (shown dashed) by a method described later. This connection is protected by a silicone rubber (or similar) moulding 88. The upper insulating sheet 72 can be made of Dacron cloth, thin Dacron reinforced silicone, PTFE or similar biocompatible insulating material. The sheet 70 in contact with the heart tissue 14 is made from thin, porous Dacron material or similar material. The two sheets 70 and 72 are joined together around the edge 90 by an adhesive (such as silicone), welded, sewn or by other means. The patches may also be made from inherently stretchy materials such as conductive polymers, or a specially knitted mesh which allows stretching and springy type of weaving, which allow deformation of the patch with the ensuing heart movement.

Figure 12:
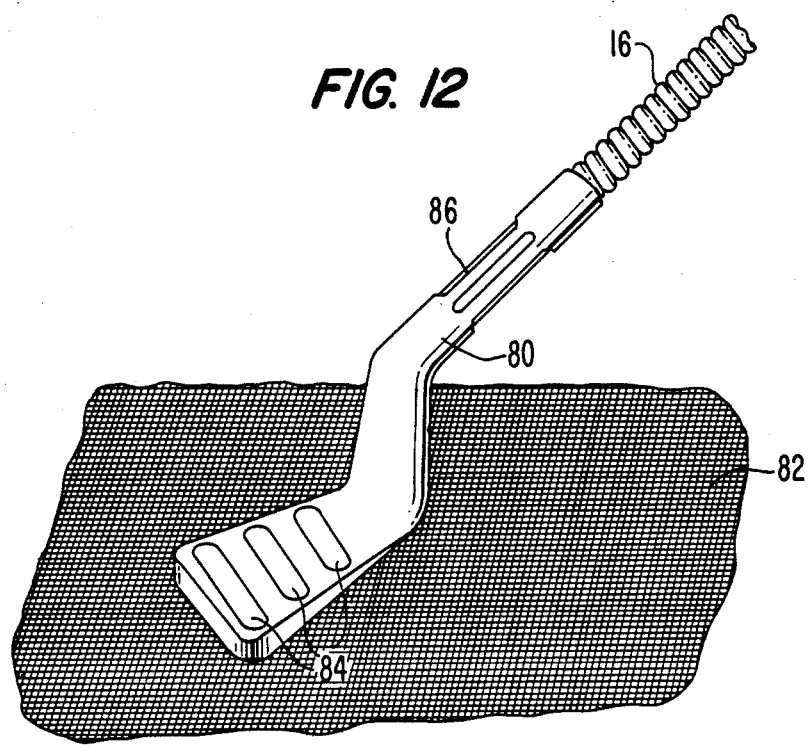
FIG. 12 is a perspective view of a spot welded connection between a connector pin and flexible sheet conductor elements of the type shown in FIGS. 8 to 11.

It is also within the spirit of this invention that the connection from the electrode patch to the conductor may vary. Hence, the connector pin 62 may change in material and shape. One type of pin 80 is shown in FIG. 12. In this case, the connector pin 80 is spot welded 84 to the patch electrode 82. The connector pin is also swaged or crimped 86 to the conductor 16. The pin 80 and the patch electrode 82 should be made of compatible materials for welding. Preferably, the two materials should be the same, such as platinum or platinum/iridium alloy. In some instances, the conductor 16 may be welded, soldered or glued with conductive adhesive directly to the electrode patch.

The presence of a patch electrode, as of any other implant material, could lead to formation of a fibrous capsule which could thicken due to excessive mechanical stress. A thick layer of insulating tissue that cannot be stimulated can also result in higher energy requirements. For these reasons it is important that the patch electrode not only have a shape and flexibility that minimize adverse tissue reaction, while allowing for rapid and firm fixation of the electrode to the heart wall, but also preferably have means for inhibiting thrombus formation in the electrode contact area. As embodied herein, and with reference to FIGS. 1 and 2, thrombus formation is prevented by the inclusion in porous layers 70, 72 of an appropriate biologically active agent such as a collagen formation inhibitor or a heart muscle cell growth stimulator, or both, naturally or artificially derived. One skilled in the art would be able to choose an appropriate agent once the selection of the porous material is made, given the present disclosure.

The above described electrode may be attached to the heart wall or pericardium during surgery using various attachment methods including the use of glue, staples, or suture barbs to actively fix the electrode to the myocardium. However, if during the surgical procedure, the pericardium is sewn back and, considering the flexibility properties of the electrode made in accordance with the present invention, active fixation may not be necessary to maintain positioning of the electrode against the heart surface.

It will be apparent to those skilled in the art that various modifications and variations could be made in the electrodes of the present invention without departing from the scope or spirit of the invention. These modifications and variations are intended to come within the scope of the appended claims and their equivalents.

What is claimed is:

1. An apparatus for use as an electrode for implantation in a patient and affixation to tissue therein having a three dimensional, time-varying surface topography, the apparatus comprising:

a tissue-contacting member including a sheet of electrically conductive, flexible material having a generally unflexed planar shape, and a plurality of elongated slits arranged in a pattern in said sheet, said slits allowing the sheet to conform to the tissue and to any movement thereof, a part of at least one interior portion of said sheet defined by said pattern being flexibly movable in a direction perpendicular to the plane of said sheet past sheet portions separated from said movable portion by said pattern of slits for continuously conforming said tissue-contacting member to the tissue during any movement of the tissue.

2. Apparatus as in claim 1 wherein said slit pattern is arranged to allow said one interior portion defined by said slit pattern to be flexibly tiltable about at least one axis lying in the plane of said sheet.

3. Apparatus as in claim 1 wherein said slit pattern is arranged to allow said one interior portion defined by said slit pattern to be flexibly tiltable about two axes lying in the plane of said sheet, said axes being mutually perpendicular to one another.

4. Apparatus as in claim 1 wherein each of said plurality of slits terminates short of the edge of said sheet, said sheet having an unslit peripheral portion.

5. Apparatus for use as an electrode adapted for implantation in a patient for contact with tissue having a time-varying, three dimensional surface topography, the apparatus comprising:

a sheet of electrically conductive flexible material having a distal surface for contacting the tissue and an opposed proximal surface; and a plurality of slits formed in said sheet in a pattern, said plurality of slits including a first pair of complementary slits extending generally in a first sheet direction, a part of the sheet portion central to said pair of slits being flexibly movable past first sheet portions separated from said central sheet portion by said first pair of slits, in a direction normal to said proximal and said distal surfaces for continuously conforming said electrically conductive flexible material to the tissue during any movement of the tissue.

6. Apparatus as in claim 5 wherein the respective ends of said slits are positioned closely adjacent one another to form opposed first web portions connecting said central sheet portion to said first separated sheet portion, and wherein said slits are arranged to allow said central sheet portion to be flexibly tiltable about an axis passing through said first web portions relative to said first separated sheet portion.

7. The apparatus as in claim 6 wherein each slit of said first pair of slits has a shape that is the mirror image of the other of said pair taken about a line passing through said first web portions.

8. Apparatus as in claim 5 wherein the shape of each of said first pair of slits is semicircular, and the shape of said central sheet portion is circular.

9. Apparatus as in claim 5 further including a second pair of complementary slits extending generally in a second sheet direction, the structural unit comprised of said first pair of slits, said included central sheet portion and said first separated sheet portion being positioned between said second pair of slits, a part of the structural unit being flexibly movable in said normal direction past a second sheet portion separated from said unit by said second pair of slits.

10. Apparatus as in claim 9 wherein said second sheet direction is perpendicular to said first sheet direction.

11. Apparatus as in claim 9 wherein said central portion is connected to said first separated sheet portion by a pair of opposed first web portions, and said first separated sheet portion is connected to said second separated sheet portions by a pair of opposed second web portions, and wherein said central sheet portion and said first separated sheet portions are independently flexibly tiltable about respective axes passing through said first and second web portions.

12. Apparatus as in claim 9 wherein said central sheet portion is circular and said first and second pairs of slits are semicircular, and wherein said second sheet direction is substantially perpendicular to said first sheet direction.

13. Apparatus as in claim 5 wherein said sheet member is concentrically shaped with respect to said central sheet member, the apparatus further including means connected to said central sheet portion for supplying an electric current to said tissue-contacting member.

14. Apparatus as in claim 5 further including a continuously porous non-conductive layer covering said proximal sheet surface and enveloping the peripheral edges of said sheet.

15. Apparatus as in claim 14 further including a second continuously porous layer covering said distal sheet surface, said second porous layer being connected to said first porous layer adjacent said sheet peripheral edges.

16. Apparatus as in claim 14 wherein said porous layer includes a biologically active agent for inhibiting thrombus formation, said agent being distributed throughout the entire porous layer.

17. Apparatus as in claim 15 wherein both said porous layer and said second porous layer include a biologically active agent for inhibiting thrombus formation, said agent being distributed throughout the respective porous layers.

18. Apparatus as in claim 15 wherein said second porous layer is less porous than said first porous layer.

19. Apparatus for use as an electrode for implantation in a patient and intended for contact with a tissue body having a time-varying, three dimensional surface topography, the apparatus comprising:

a generally planar electrically conductive tissue contacting member, said member having (i) an annular peripheral portion, (ii) an annular intermediate portion positioned concentric with, and spaced from, said peripheral portion, said intermediate portion being connected to said peripheral portion by a pair of opposed outer web portions, and (iii) a central portion positioned concentric with, and spaced from, said intermediate portion, said central portion being connected to said intermediate portion by a pair of opposed inner web portions, said peripheral, intermediate, and central portions being flexibly movable with respect to one another in a direction normal to the plane of said tissue contacting member for continuously conforming said member to the tissue during any movement of the tissue.

20. Apparatus as in claim 19 wherein a line drawn through said pair of outer web portions is angularly displaced from a line drawn through said pair of inner web portions.

21. Apparatus as in claim 19 wherein said inner and outer web portions are reduced in width, said outer web portions formed to allow said intermediate portion to be flexibly tiltable about a first axis passing through said outer web portions, and said inner web portions formed to allow said central portion to be flexibly tiltable about a second axis passing through said inner web portions.

22. An apparatus for use as an electrode for implantation in a patient and affixation to tissue therein having a three dimensional, time-varying surface topography, the apparatus comprising:
a tissue-contacting member including a sheet of electrically conductive, flexible material having a generally unflexed planar shape and disposed in a spiral pattern for continuously conforming said tissue-contacting member to the tissue during any movement of the tissue.

23. Apparatus as recited in claim 22, wherein said member has a distal surface for contacting the tissue and the apparatus further comprises a continuously porous layer covering said distal surface.

24. Apparatus as recited in claim 22, wherein said member has a distal surface for contacting the tissue and an opposed proximal surface, the apparatus further comprising a non-conductive layer covering said proximal surface.

25. An apparatus for use as an electrode for implantation in a patient and affixation to tissue therein having a three dimensional, time-varying surface topography, the apparatus comprising:
flexible conductive means for providing electrical contact with the tissue once said apparatus is implanted in a patient, said means once implanted continuously contacting the tissue during any movement of the tissue and being disposed in a spiral pattern on the tissue; and
a porous layer providing on one side of said flexible means to facilitate secure affixation of said flexible means to the tissue.

26. Apparatus recited in claim 25, wherein said porous layer comprises a Dacron material.

27. An apparatus for use as an electrode for implantation in a patient and affixation to tissue therein having a three dimensional, time-varying surface topography, the apparatus comprising:
a tissue-contacting member including a sheet of electrically conductive, flexible material having a generally unflexed planar shape,
said sheet including a pattern of slits that define a plurality of conductive regions interconnected by web portions, with each of said conductive regions being coupled to adjacent ones of said conductive regions by no more than a total of two of said web portions.

28. Apparatus as recited in claim 27, wherein each of said conductive regions is substantially circular in shape.

29. Apparatus as recited in claim 28, wherein said conductive regions are concentrically arranged, with each of said conductive regions being connected to adjacent conductive regions via two of said web portions.

30. Apparatus as recited in claim 27, wherein one of said conductive regions is centrally located within said tissue-contacting member, with the other ones of said conductive regions being disposed radially about said centrally located conductive region.

31. Apparatus as recited in claim 30, wherein said centrally located conductive region is individually connected to each of said radially disposed conductive regions via one of said web portions.

32. Apparatus as recited in claim 27, wherein one of said conductive regions is centrally located within said tissue-contacting member, with another one of said conductive regions being disposed spirally about said centrally located conductive region.

33. Apparatus as recited in claim 32, wherein said centrally located conductive region is connected to said spirally disposed conductive region via one of said web portions.

* * * * *